United States Patent [19]

Nerome et al.

[11] Patent Number: 5,176,909
[45] Date of Patent: Jan. 5, 1993

[54] STABLE IMMUNOGEN COMPOSITION FOR ORAL ADMINISTRATION

[75] Inventors: Kuniaki Nerome, Tokyo; Kuniharu Seki; Katsuhiko Ohyama, both of Yokohama, all of Japan

[73] Assignee: The Nisshin Oil Mills, Ltd., Tokyo, Japan

[21] Appl. No.: 590,230

[22] Filed: Sep. 28, 1990

[30] Foreign Application Priority Data

Sep. 29, 1989 [JP] Japan .................................. 1-256472

[51] Int. Cl.⁵ .......................... A61K 39/00; A61K 9/16
[52] U.S. Cl. .......................................... 424/88; 424/89;
424/92; 424/492; 530/350; 530/395; 530/413; 530/416; 530/427; 530/806
[58] Field of Search ...................... 424/88, 89, 92, 492; 530/350, 395, 413, 416, 427, 806

[56] References Cited

U.S. PATENT DOCUMENTS

| | | | |
|---|---|---|---|
| 4,376,113 | 3/1983 | Suglia et al. | 424/92 |
| 4,987,031 | 1/1991 | Tatematsu et al. | 424/492 |

FOREIGN PATENT DOCUMENTS

| | | |
|---|---|---|
| 621398 | 2/1963 | Belgium . |
| 0142193 | 10/1984 | European Pat. Off. . |
| 037971 | of 1980 | Japan . |
| 502262 | of 1987 | Japan . |
| 1198513 | 7/1970 | United Kingdom . |
| 2144331 | 3/1985 | United Kingdom . |
| WO83/03102 | 9/1983 | World Int. Prop. O. . |

OTHER PUBLICATIONS

M. Kurokawa, S. Ishida, R. Murata, A. Oya, T. Sawada, S. Kameyama, and S. Ohtani "Accelerated degradation tests on some immunological products", 1979, pp. 31-41.

Ker-Sang Chen and Gerald V. Quinnan, Jr., "Secretory Immunoglobulin A Antibody Response Is Conserved in Aged Mice following Oral Immunization with Influenza Virus Vaccine", 1989, pp. 3291-3296.

Robert H. Waldman, Karl-Christian Bergmann, Judy Stone, Stephen Howard, Vince Chiodo, Arthur Jacknowitz, Elizabeth R. Waldman, and Rashida Khakoo, "Age-Dependent Antibody Response in Mice and Humans Following Oral Influenza Immunization", 1987, pp. 327-332.

*Primary Examiner*—Johnnie R. Brown
*Assistant Examiner*—Abdel A. Mohamed
*Attorney, Agent, or Firm*—Bryan Cave

[57] ABSTRACT

A stable immunogen composition for oral administration which includes a dried spherical form comprised of an immunogen capable of immunizing human or animals and a gelatin having an average molecular weight of 80,000–120,000 and jelly strength of more than 150 (Bloom, g, 6.2/3%), and is enteric.

14 Claims, 7 Drawing Sheets

STABLE IMMUNOGEN COMPOSITION FOR ORAL ADMINISTRATION

BACKGROUND OF THE INVENTION

1. Field of the Invention

The present invention relates to a stable immunogen composition for oral administration.

2. Prior Art

An immunogen capable of immunizing human or animals is usually suspended in a buffered physiological saline for use. Such a suspension is referred to as vaccine. Examples of known vaccines are inactivated vaccines such as typhoid vaccine, pertussis vaccine, rabies vaccine and the like, attenuated live vaccines such as pathogenic micro-organism vaccine, live polio vaccine and the like, and toxoids such as diphtheria toxoid, tetanus toxoid and the like. An immunogen can be easily inactivated by physical factors such as temperature, light, shaking and the like since it consists mainly of proteins. Hence special care has been needed for preparation and storage of vaccines. It is known that saccharide or water-soluble gelatin (molecular weight: less than 20000) is added to a vaccine so as to improve in stability during storage.

Since vaccines are usually administered by injection, they tend to cause side effects such as redness, fever and amyotrophia in the administered region, shock and the like, beside being inconvenient administration.

In order to solve this problem, dosage forms of vaccine for oral administration have been proposed. A typical example of such dosage form is a powder or tablet preparation in which an immunogen is supported on a solid carrier such as lactose, saccharose and the like (Japanese Published Examined Patent Application No. 502262/1987). Further, it is known that cytochrome C, which is not an immunogen, is treated with gelatin of molecular weight of more than 50000 to form a composite material which is then formulated into various types of preparations for oral administration (Japanese Published Examined Patent Application No. 37971/1980).

SUMMARY OF THE INVENTION

An object of the invention is to provide a preparation for oral administration which allows an immunogen to be orally administered thereby to overcome various problems ascribed to a preparation for injection, while potency of the immunogen is not lowered.

According to the present invention, there is provided a stable immunogen composition for oral administration which comprises a dried spherical form comprising an immunogen capable of immunizing human or animals and a gelatin having an average molecular weight of 80,000–120,000 and jelly strength of more than 150 (Bloom, g, 6·⅔%), and is enteric.

DESCRIPTION OF THE PREFERRED EMBODIMENTS

Figure 1:
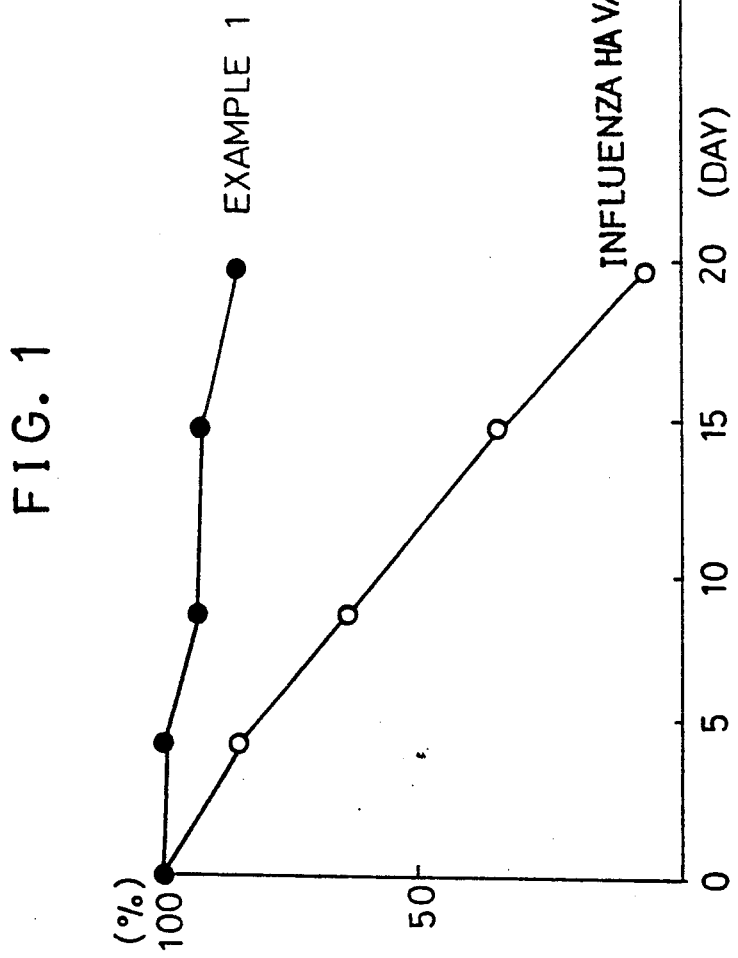
FIG. 1 is a graph comparing the change in the antigenic potency of the dried spherical form of Example 1 with that of the influenza HA vaccine.

In the present invention, the term "an immunogen capable of immunizing human or animals" as recited above includes all the immunogens that can be utilized for preventing infectious diseases. Examples thereof are inactivated vaccines (influenza, Japanese encephalitis, pertussis, triple vaccine, cholera, pneumococcus and the like), attenuated live vaccines (polio, measles, rubella, mumps, BCG, typhoid, variola and the like), toxoids (diphtheria, tetanus, trimeresurus toxoid, typhoid, botulinus and the like), and component vaccines (influenza HA, hepatitis B, non-A, non-B hepatitis, herpes and the like).

The composition of the invention can be prepared from a buffered physiological saline containing an immunogen. Freeze-drying method for stabilizing the live polio vaccine is known, but we found that such freeze-dried lyophilized vaccine is not suitable to use as a raw material in the invention.

Gelatin constituting the composition of the invention is required to have 80,000–120,000 of average molecular weight and more than 150 of jelly strength (Bloom, g, 6·⅔%). Even if the average molecular weight resides within the above range, jelly strength of less than 150 cannot give a composition of desired stability. The maximum jelly strength of gelatin used is approximately 340, and preferable strength thereof is approximately 300. Raw materials for the gelatin are not limited, provided that the above conditions are satisfied.

The composition of the invention can be made by adding the gelatin to a buffered physiological saline containing an immunogen, mixing at a low temperature (for example, 0°–10° C., preferably 4°–5° C.) and warming (e.g., below 50° C., preferably below 40° C.) to give a sol. The composition in a sol state is dropped to a physiologically non-toxic liquid which is non-compatible with water and of which specific gravity is smaller than that of water (for example, castor oil, camellia oil, soybean oil, liquid paraffin and the like), thereby becoming a flexible spherical form. In this case, it is preferable that the sol is maintained under warming and the above liquid is warmed at its upper portion while being cooled at its lower portion (for example, 0°–10° C.).

The flexible spherical form thus obtained is gradually dried under atmospheric pressure at a low temperature (for example, 0°–10° C., preferably 4°–5° C.) to give a solid spherical form. Diameter of the solid spherical form is not particularly limited, but preferably 0.5–2.0 mm. Dryness of the spherical form is preferably less than 30% of water content thereof, more preferably 20–10%.

The spherical form thus obtained can be directly coated with an enteric coating agent which is appropriately selected from known ones in the art. Preferable examples of the enteric coating agent are methacrylic acid copolymer, hydroxypropylmethyl cellulose phthalate, hydroxypropylmethyl cellulose acetate succinate, carboxymethylethyl cellulose, cellulose acetate phthalate, purified shellac, white shellac, ethyl cellulose, aminoalkyl methacrylate copolymer, methacrylic acid copolymer.

The coating can be performed by a film coating method using a flow coater or centrifugal granulator. The enteric spherical form thus obtained is used as a preparation for oral administration. Instead of the above process, pharmaceutically acceptable excipient or diluent, binder and the like may be added to the spherical form (without enteric coating) to form a tablet, followed by being coated with the enteric coating agent. Otherwise, the above spherical form may be put into an enteric capsule to form a capsulated preparation.

Where the spherical form of the invention is prepared, it is required to use a small amount of immunogen relative to the amount of gelatin to be used. The amount of immunogen depends on the kind of immunogen to be used, but generally preferred is about 1/50–1/100,000,000 relative to 1 weight part of gelatin. According to the above method, stability of the immunogen can be assured. Conceivably, this is because the immunogen is sealed with gelatin with its configuration (especially, configuration of antigenic determinant existing in virus, microorganism or dead microorganism) maintained and without chemically bonding. It has been confirmed that the immunogen does not form a conjugate with gelatin.

The composition of the invention may contain an adjuvant. It is preferable to use a muramylpeptide derivative (disclosed in, for example, European laid-open Patent Application No. 0316934A2) or a lipid-A analog. Addition of such adjuvant enhances effectiveness of the composition of the invention and reduces variation in effect thereof depending on individual differences.

Where the composition of the invention is orally administered, the enteric coating, then gelatin are dissolved at intestine to release the immunogen therein, followed by being absorbed from enteric canal. Conceivably, immunization occurs at Peyer's patches existing in enteric canal.

The amount of the composition to be orally administered depends greatly on the kind of immunogen used. For example, in the case of influenza, usually 50–20,000 CCA (Chich Red Cell Agglutination)/grown-up person is orally administered for one administration and optionally administered in the same manner 2–4 weeks after the first administration. In the case of hepatitis B, usually 0.1–1.0 mg as antigen protein/grown-up person is orally administered as the first administration, the second administration is carried out 4 weeks after the first administration, and the third administration is carried out 20–24 weeks after the first administration. Thus, the administration is carried out three times. In the case of Japanese encephalitis, 10–1,000 μg as antigen protein is orally administered to a person of more than 6 months after birth twice with 1–2 week interval.

EXAMPLES

The present invention will be fully described with reference to Examples which are not intended to limit the invention.

Example 1

(1) Preparation of a dried spherical form

Gelatin powder [20 g, jelly strength: 300 (Bloom, g, 6.⅜%), average molecular weight: about 100,000, NIPPI Co., Ltd.] was added to influenza HA vaccine (80 ml, 200 μg/ml as protein, HA potency: 14000) and mixed at 4° C. The mixture was heated to 40° C. while stirring to reach a sol state. On the other side, 1000 ml of soybean oil was poured into a 1000 ml graduated cylinder, then the upper portion thereof (10 cm from the liquid level) was heated to 40°–50° C. while the lower portion thereof (50 cm from the bottom) was cooled to 4° C. Using 20 ml syringe of 2 mm diameter, the sol-state mixture maintained at 40° C. was dropped to the graduated cylinder filled with soybean oil, followed by standing for 30 minutes. Only a gelated spherical form thus obtained was moved from the graduated cylinder to a beaker, then washed with cooled acetone to remove the soybean oil. Further, the spherical form was washed with 5000 ml of cooled water about ten times repeatedly, and finally washed with 1000 ml of aqueous solution of alcohol (60%). The gelated spherical form thus obtained was dried for 4–5 days in a temperature controlled bath at 4° C. to give a dried spherical form of 0.5–2 mm diameter with water content of 15% relative to that of the gelated spherical form.

(2) Electrophoresis

In electrophoresis using SDS-polyacrylamide gel with respect to the above gelatin, influenza HA antigen and dried spherical form prior to film coating, it was confirmed that the gelatin showed a broad spot, the influenza HA antigen showed a single spot, and the dried spherical form showed two spots at coincident spot locations of the gelatin and the influenza HA antigen.

From the above, it is judged that the gelatin and influenza HA antigen did not form an conjugate.

(3) Enteric coating

The dried spherical form was then coated with enteric film coat of the following recipe of Table 1.

TABLE 1

| Recipe of enteric film coat | |
|---|---|
| methacrylic acid copolymer L | 5 weight parts |
| polyethylene glycol 400 | 0.5 weight parts |
| ethanol | 45 weight parts |
| dichloromethane | 45 weight parts |
| water | 4.5 weight parts |
| Total | 100 weight parts |

Examples 2-6

In the same manner as in Example 1, using hepatitis B vaccine, Japanese encephalitis vaccine, pertussis vaccine, non-A, non-B hepatitis vaccine and influenza inactivated vaccine of the concentrations shown in Table 2, respective dried spherical forms and film-coated dried spherical forms were obtained.

TABLE 2

Concentrations of vaccines used for preparations

| Example | Vaccine | Concentration used for preparation (μg/ml · protein) |
|---------|---------|------------------------------------------------------|
| 2 | hepatitis B | 30 μg/ml · protein |
| 3 | Japanese encephalistis | 50 μg/ml · protein |
| 4 | pertussis | 80 μg/ml · protein |
| 5 | non-A, non-B hepatitis | 10 μg/ml · protein |
| 6 | influenza (inactivated) | 600 μg/ml · protein |

Examples 7-10

In the same manner as in Example 1, dried spherical forms were obtained using influenza HA vaccine and gelatin (average molecular weight about 100,000) of different jelly strengths.

Each dried spherical form (0.1 g) was dissolved in 5 ml of phosphate buffer containing collagenase to perform HA (hemagglutinin) test using chicken erythrocyte for measuring antigen potency thereof.

The result of the test is shown in Table 3, and according thereto, any dried spherical form obtained using gelatin of more than 150 jelly strength maintained sufficient HA potency.

TABLE 3

| Example | jelly strength | HA potency (average of 3 cases) |
|---------|----------------|---------------------------------|
| comparative Example | 100 | 16.0 |
| 7 | 150 | 85.3 |
| 8 | 200 | 85.3 |
| 9 | 250 | 106.7 |
| 10 | 300 | 106.7 |

Example 11

Instead of obtaining the dried spherical form (water content 15% relative to that of the gelated spherical form), dried spherical forms of respective water contents of 30%, 40% and 50% relative to that of the gelated spherical form were prepared.

HA test was performed with respect to each dried spherical form having stood for 20 days at 40° C. Consequently, the dried spherical form of 30% water content exhibited 106.7 HA potency, while the dried spherical form of Example 1 exhibited 128.0 HA potency.

In contrast, the dried spherical forms of 40% and 50% water contents exhibited 64.0 and 42.7 HA potency, respectively, which turned out to be unsuitable.

Example 12

A dried spherical form containing influenza HA was prepared in the same manner as in Example 1 except that muramyldipeptide of 100 μg/ml concentration was added as an adjuvant.

HA test was performed with respect to this dried spherical form, resulting in 106.7 HA potency. Substantial decrease in HA potency was not recognized from the result of the test (refer to Example 10).

Stability Test

Figure 2:
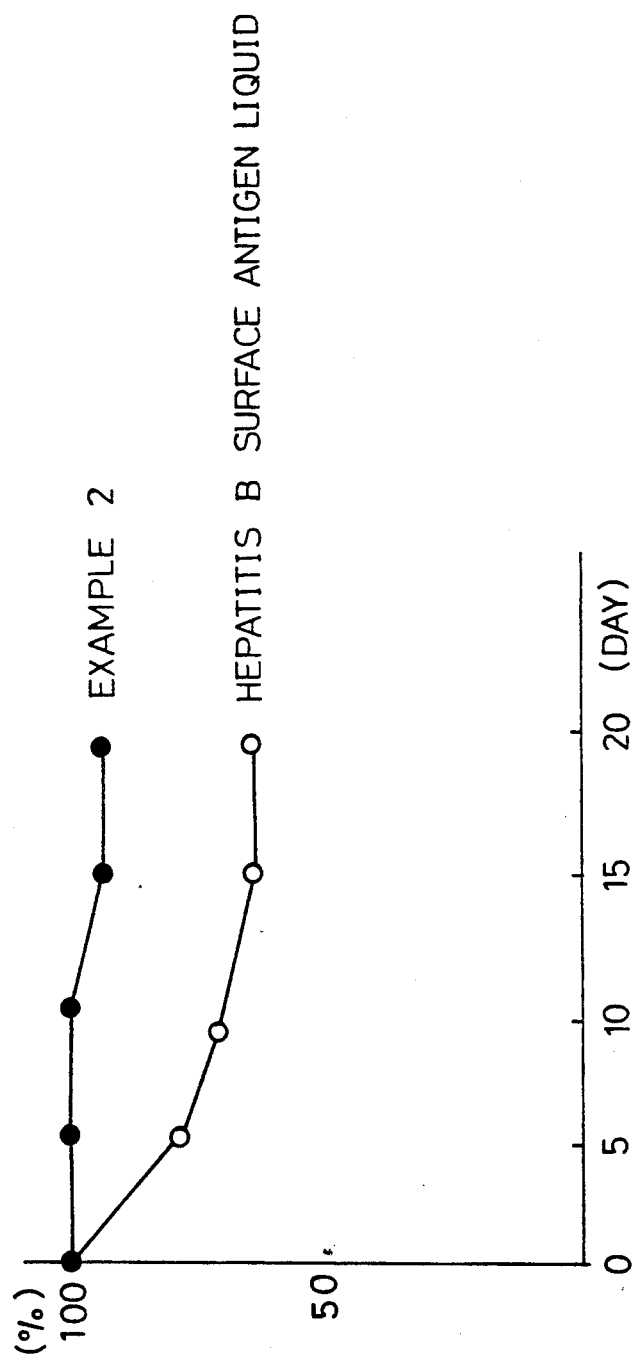
FIG. 2 is a graph comparing the change in the antigenic potency of the dried spherical form of Example 2 with that of the hepatitis B surface antigen liquid vaccine.
Figure 3:
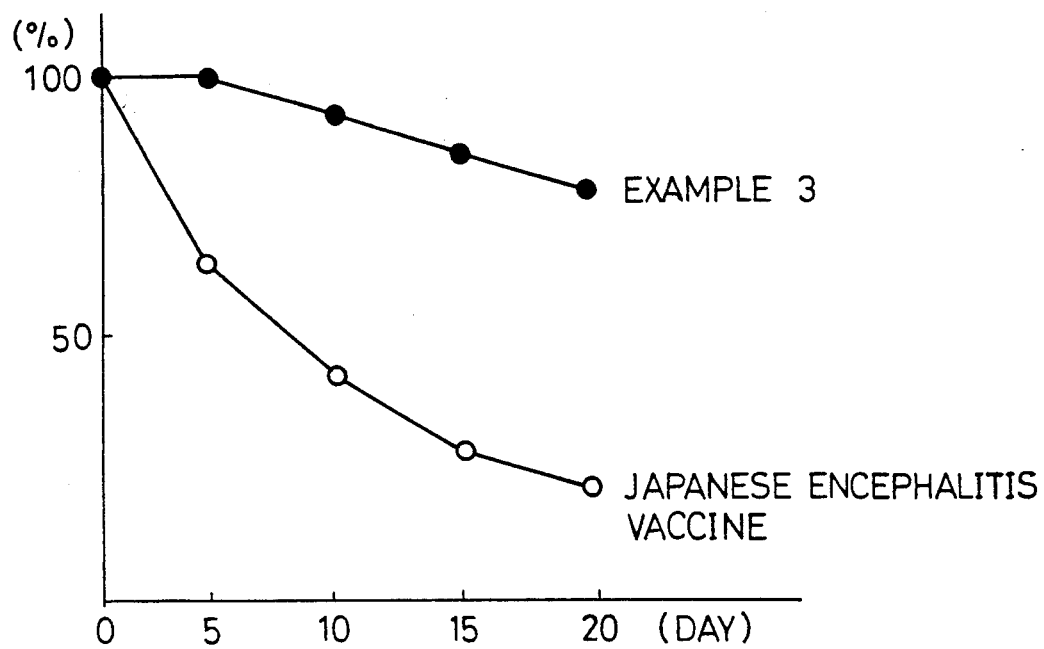
FIG. 3 is a graph comparing the change in the antigenic potency of the dried spherical form of Example 3 with that of the Japanese encephalitis vaccine.
Figure 4:
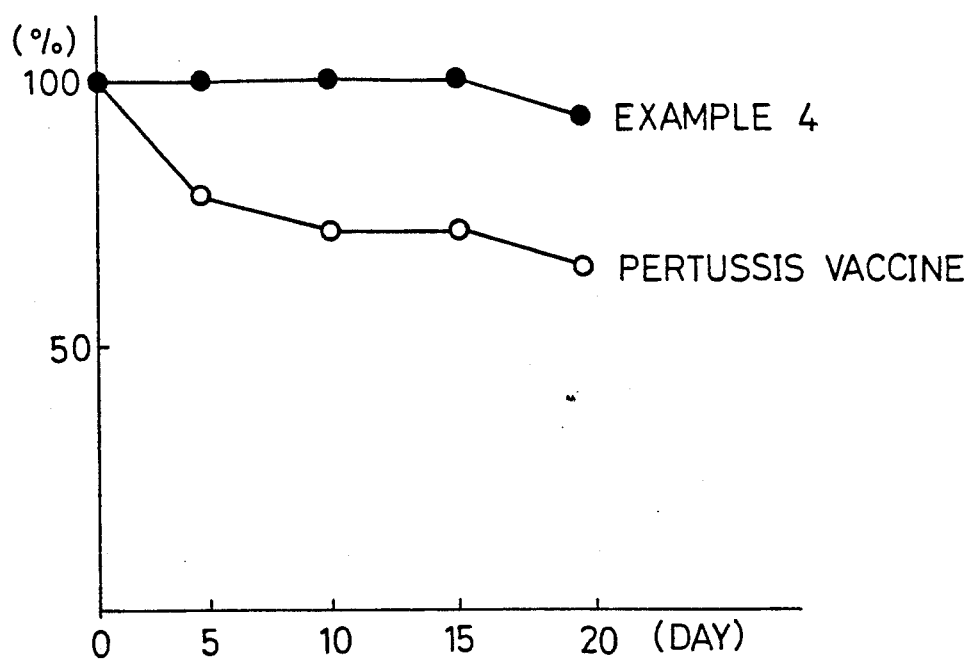
FIG. 4 is a graph comparing the change in the antigenic potency of the dried spherical form of Example 4 with that of the pertussis vaccine.
Figure 5:
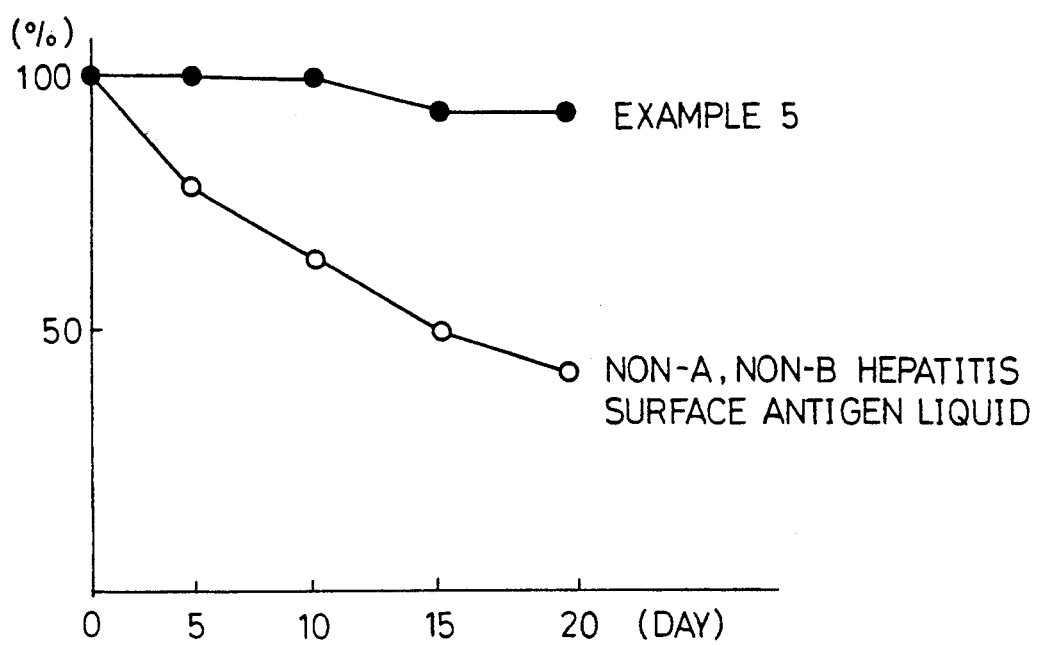
FIG. 5 is a graph comparing the change in the antigenic potency of the dried spherical form of Example 5 with that of the non-A, non-B hepatitis surface antigen liquid vaccine.
Figure 6:
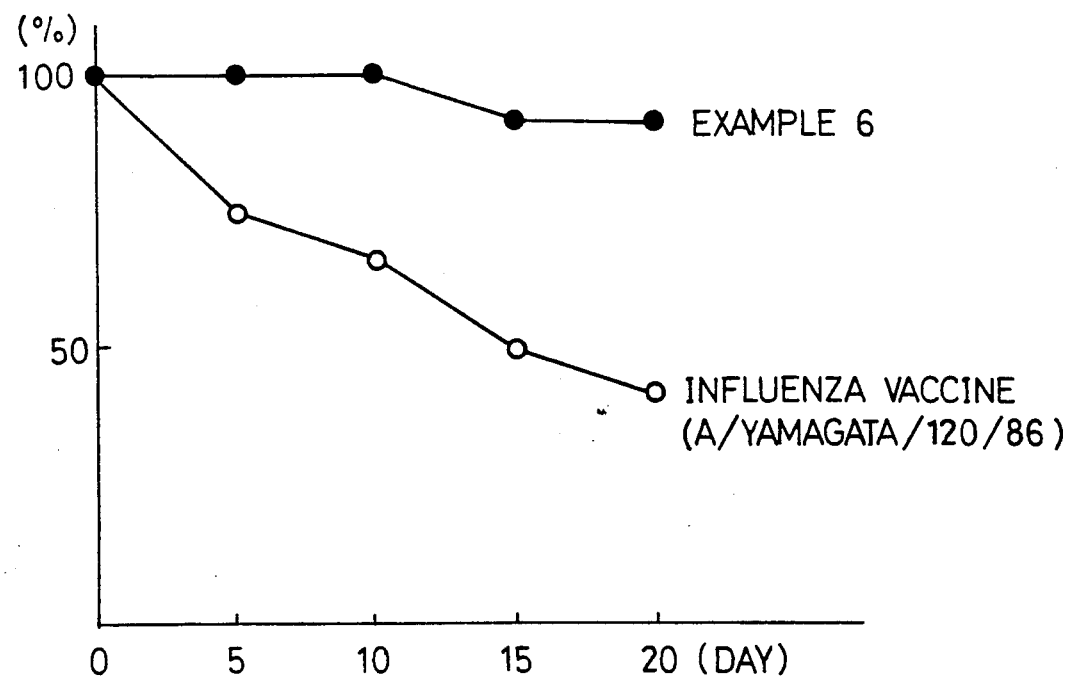
FIG. 6 is a graph comparing the change in the antigenic potency of the dried spherical form of Example 6 with that of the influenza (inactivated) vaccine.

Antigen potency retentions in the period of standing at 40° C. of the dried spherical forms (prior to film coating) obtained in Examples 1-6 were measured. Each of the corresponding vaccines used as raw materials for respective dried spherical forms was also measured in antigen potency retention for comparison. As shown in FIGS. 1-6, antigen was stably maintained in any of the dried spherical forms of Examples 1-6.

Immunity Test

Figure 7:
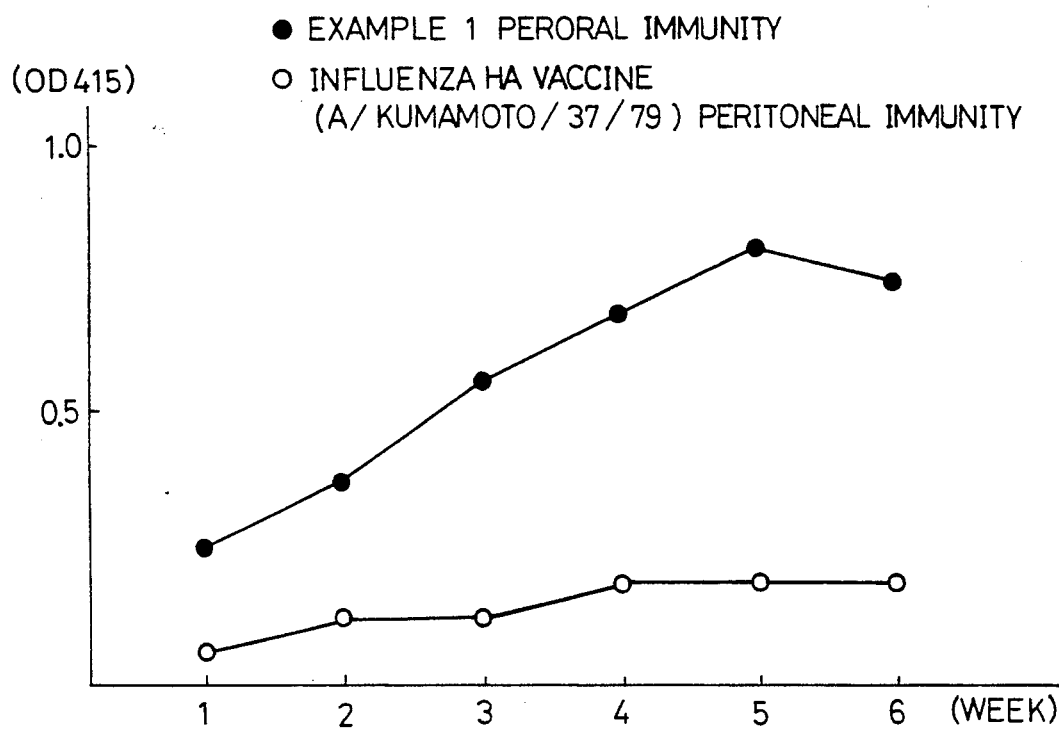
FIG. 7 is a graph comparing the immunoactivity of the dried spherical form of Example 1 after standing for 20 days at 40° C. with the immunoactivity of the influenza HA vaccine after standing for 20 days at 40° C.
Figure 8:
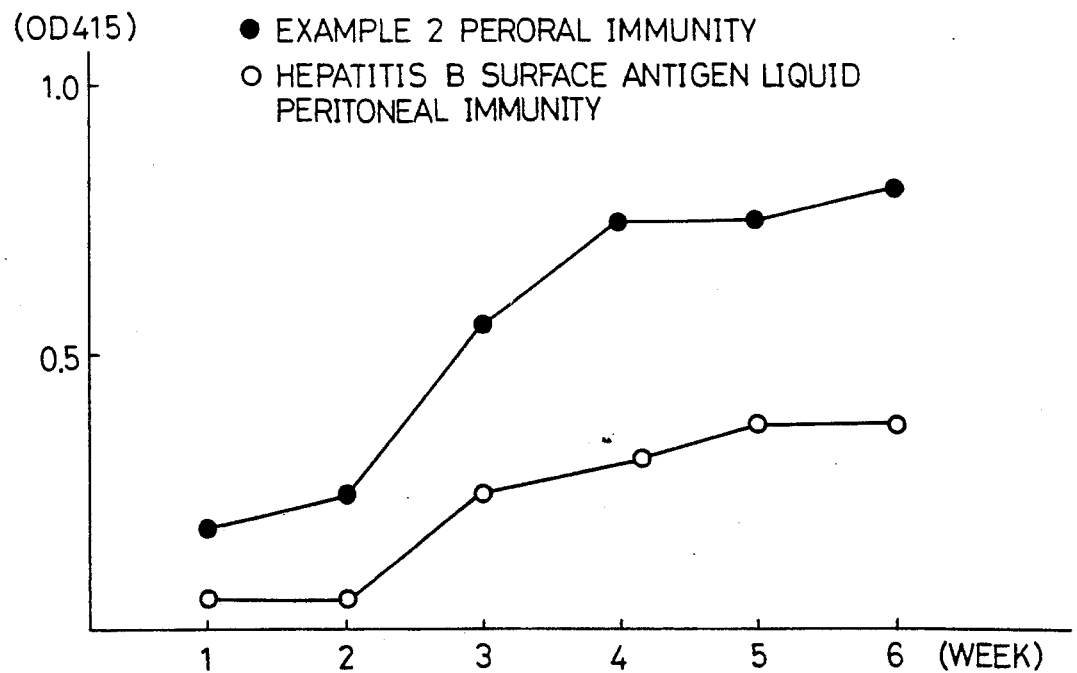
FIG. 8 is a graph comparing the immunoactivity of the dried spherical form of Example 2 after standing for 20 days at 40° C. with the immunoactivity of the hepatitis B surface antigen liquid vaccine after standing for 20 days at 40° C.
Figure 9:
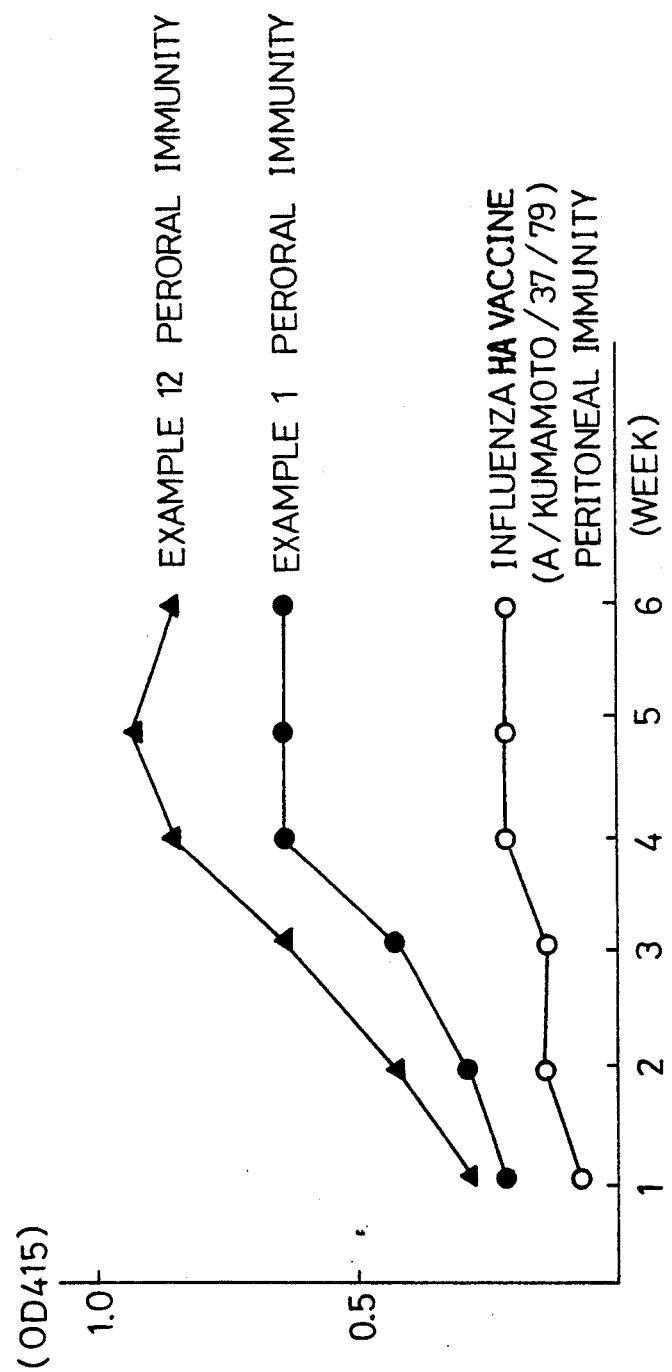
FIG. 9 is a graph comparing the immunoactivity of the dried spherical forms of Examples 1 and 12 after standing for 20 days at 40° C. with the immunoactivity of the influenza HA vaccine after standing for 20 days at 40° C.
Figure 10:
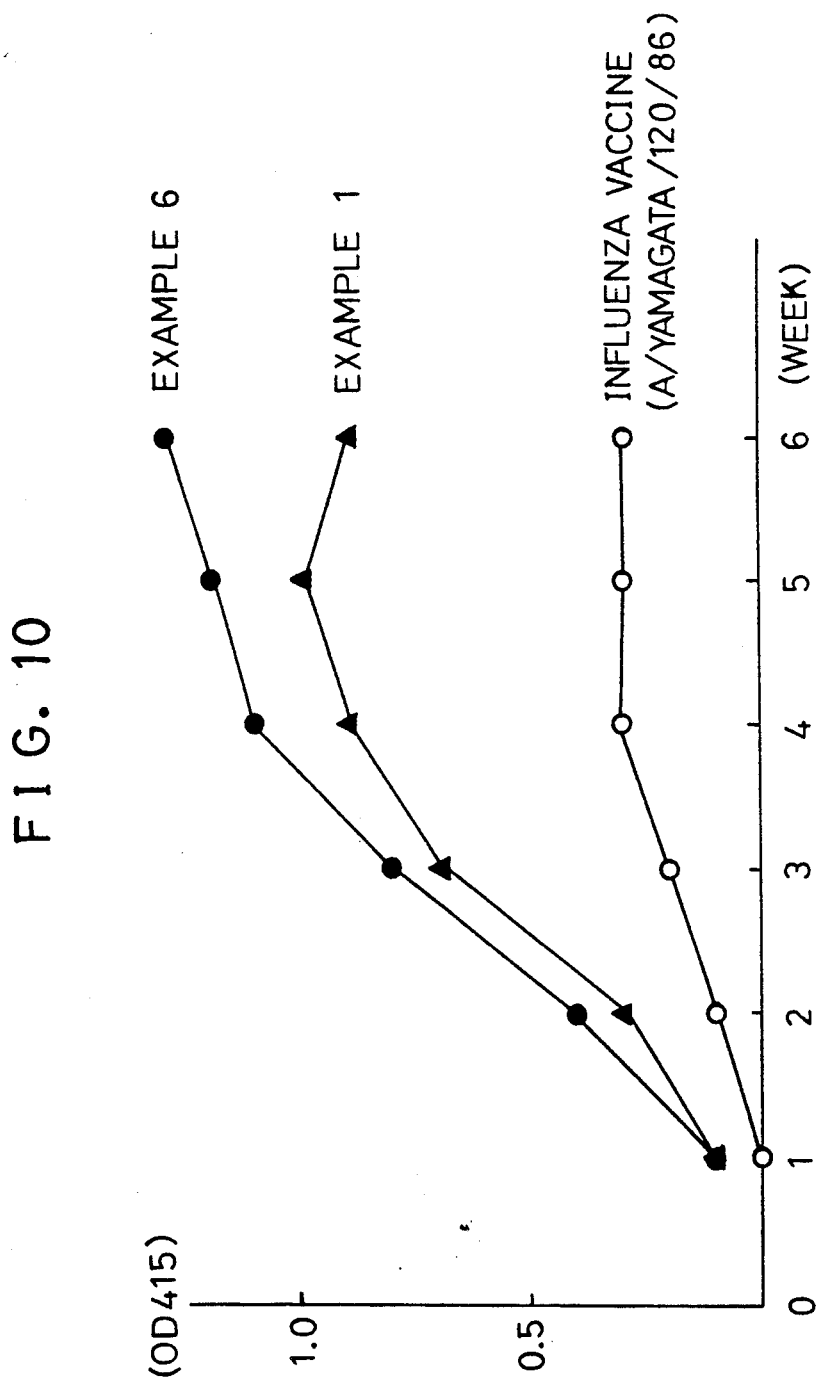
FIG. 10 is a graph comparing the immunoactivity of the dried spherical forms of Examples 1 and 6 after standing for 20 days at 40° C. with the immunoactivity of the influenza (inactivated) vaccine after standing for 20 days at 40° C.

The dried spherical forms of Examples 1, 2, 6 and 12 were subjected to film coating, then allowed to stand for 20 days at 40° C. Thereafter, immunity test was performed in the following manner. Mice were orally immunized with respective dried spherical forms, then blood collection was performed for them once every week. The amount of IgG antibody existing in each serum of the collected bloods was measured by ELISA method. The result was shown in FIGS. 7-10 on the basis of absorbance at 415 nm wavelength. For comparison used were corresponding vaccines having respectively used for preparing the above dried spherical forms.

Example 13

Enteric Coating

The spherical form of the invention was coated with an enteric film of the following recipe in an amount of 15% relative to that of the spherical form.

| | |
|---|---|
| hydroxypropyl methylcellulose acetate succinate | 2.5 weight parts |
| shellac | 0.5 weight parts |
| talc | 0.3 weight parts |
| glycerol ester of fatty acid | 0.3 weight parts |
| ethanol | 25.0 weight parts |
| dichloroethane | appropriate amount |
| Total | 100 weight parts |

Example 14

The dried spherical form of the invention was coated with an enteric coating agent of the following recipe in an amount of 10% relative to that of the dried spherical form.

| | |
|---|---|
| hydroxypropyl methylcellulose phthalate | 5.0 weight parts |
| shellac | 0.5 weight parts |
| glycerol ester of fatty acid | 0.5 weight parts |
| ethanol | 45.0 weight parts |
| dichloroethane | appropriate amount |
| Total | 100 weight parts |

Then, the coated dried spherical form was overcoated with a film of the following recipe in an amount of 10% relative to that of the dried spherical form.

| | |
|---|---|
| hydroxypropyl methylcellulose acetate succinate | 2.5 weight parts |
| shellac | 0.5 weight parts |
| talc | 0.3 weight parts |
| glycerol ester of fatty acid | 0.3 weight parts |
| ethanol | 25.0 weight parts |
| dichloroethane | appropriate amount |

-continued

| | |
|---|---|
| Total | 100 weight parts |

Example 15

The following components were compressed.

| | |
|---|---|
| dried spherical form | 20 weight parts |
| lactose | 70 weight parts |
| starch | appropriate amount |
| magnesium stearate | 0.5 weight parts |
| Total | 100 weight parts |

Then, the tablet thus obtained was coated with an enteric film of the same recipe as in Example 1 in an amount of 5% by weight relative to that of the tablet.

What is claimed is:

1. A stable immunogen composition for oral administration which comprises a dried spherical form comprising an immunogen which immunizes humans or animals and a gelatin having an average molecular weight of 80,000-120,000 and jelly strength of from 150 to 340 (Bloom, g. 6-$\frac{2}{3}$%), and is enteric, wherein an amount of the immunogen used is 1/50-1/100,000,000 by weight relative to that of the gelatin.

2. The composition as set forth in claim 1, wherein the immunogen is selected from the group consisting of influenza, Japanese encephalitis, hepatitis B, pertussis, non-A hepatitis, and non-B hepatitis.

3. The composition as set forth in claim 1, wherein the dried spherical form is coated with an enteric film.

4. The composition as set forth in claim 1, wherein the dried spherical form is capsulated with an enteric capsule.

5. The composition as set forth in claim 1, wherein the dried spherical form is in the form of a tablet and said tablet is enteric.

6. The composition as set forth in claim 1, which contains an adjuvant which enhances immunity of the immunogen.

7. A process for the preparation of a stable immunogen composition for oral administration which comprises adding a gelatin having 80,000-120,000 of average molecular weight and from 150 to 340 of jelly strength (Bloom, g, 6-$\frac{2}{3}$%) to a buffered physiological saline solution comprising an immunogen, mixing the mixture at a low temperature in the range of from 0° to 10° C., warming the mixture at a temperature in the range of from 40° C. to 50° C. to give a dispersion of solid particles in a liquid colloidal solution, pouring the dispersion of solid particles in a liquid colloidal solution into a physiologically non-toxic liquid which is non-compatible with water to give a flexible spherical form, drying the flexible spherical form at a low temperature in the range of from 0° C. to 10° C. to give a solid spherical form which is enteric.

8. The process as set forth in claim 7, wherein the physiologically non-toxic liquid is selected from the group consisting of castor oil, camellia oil, soybean oil, and liquid paraffin.

9. The process as set forth in claim 7, for preparing a composition wherein the immunogen is in the amount of 1/50-1/100,000,000 by weight relative to the amount of the gelatin.

10. The process as set forth in claim 7, for preparing a composition wherein the immunogen is selected from the group consisting of influenza, Japanese encephalitis, hepatitis B, pertussis, non-A hepatitis, and non-B hepatitis.

11. The process as set forth in claim 7, for preparing the composition further comprising coating the dried spherical form with enteric film.

12. The process as set forth in claim 7, for preparing the composition further comprising encapsulating the dried spherical form with an enteric capsule.

13. The process as set forth in claim 7, for preparing the composition further comprising forming the dried spherical form into an enteric tablet.

14. The process as set forth in claim 7, for preparing the composition containing an adjuvant which enhances immunity of the immunogen.

* * * * *